United States Patent
Tsou

Patent Number: 5,966,919
Date of Patent: Oct. 19, 1999

[54] AUTOMATIC COMPOSITE YARN DETECTOR

[76] Inventor: Li Kuo Tsou, 5th Fl., No. 1, Lane 538, Chung Cheng Rd., Shin-den, Taipei, Hsien, Taiwan

[21] Appl. No.: 09/071,783

[22] Filed: May 1, 1998

[51] Int. Cl.[6] ..................................................... D01H 7/46
[52] U.S. Cl. .............................................. 57/264; 73/160
[58] Field of Search ....................... 57/264, 265; 73/160, 73/760; 28/248, 178, 185, 186, 187, 188, 194; 425/169, 170, 171; 324/698

[56] References Cited

U.S. PATENT DOCUMENTS

| | | |
|---|---|---|
| 4,300,094 | 11/1981 | Piso et al. .................................. 324/65 |
| 4,479,979 | 10/1984 | Prober ........................................... 427/9 |
| 5,768,938 | 6/1998 | Schilling et al. ........................... 73/160 |

*Primary Examiner*—William Stryjewski
*Assistant Examiner*—Gina Silverio
*Attorney, Agent, or Firm*—Notaro & Michalos P.C.

[57] ABSTRACT

An automatic composite yarn detector including a housing having a passage way through which the yarn to be tested passes, two electrically conductive contact elements intersecting the passage way to receive the pressure of the yarn and to detect its oil content, a tension feeler connected to the contact elements and induced by the pressure received by the contact elements to provide an output signal, and a processing circuit adapted to process the yarn tension signal detected by the tension feeler and the oil content signal detected by the contact elements into corresponding output signals for display through an external display.

10 Claims, 4 Drawing Sheets

5,966,919

AUTOMATIC COMPOSITE YARN DETECTOR

BACKGROUND OF THE INVENTION

The present invention relates to an automatic composite yarn detector for automatically detecting the tension and oil content of a composite yarn.

A yarn is basic material used in textile industry for weaving into a variety of fabrics. Therefore, the quality of yarns used in weaving have a great concern with the quality of finished fabrics. In a regular pseudo twist machine, a tension feeler is provided for detecting the tension of the yarn, so that the quality of the finished yarn can be controlled. It is known that during a high speed yarn spinning process either FDY, POY or FOY, or a pseudo twisting process, an individual filament of the dragged yarn may be broken or stretched to produce a static electricity, causing the quality of the yarn to be affected. In order to prohibit the occurrence of this problem, an oil is applied to the yarn during the spinning process. However, the amount of the oil applied must be properly controlled so as not to affect the quality of the yarn. Further, the uniformity of the chemically reacted particle crystal will affect the strength, extensibility and elastic resilient power of the yarn. However, these properties can only be examined by sampling inspection, i.e., by examining the quality of one sample sampled from about one million of finished yarns. This examination procedure requires much time and labor.

SUMMARY OF THE INVENTION

The present invention has been accomplished under the circumstances in view. It is one object of the present invention to provide an automatic composite yarn detector which is compact and easy to operate. It is another object of the present invention to provide an automatic composite yarn detector which simultaneously detects the tension of the yarn and its oil content. It is still another object of the present invention to provide an automatic composite yarn detector which permits the operator to monitor the detection during the yarn spinning process. It is still another object of the present invention to provide an automatic composite yarn detector which permits the operator to adjust the yarn tension detecting range and the oil content detecting range as desired. According to one aspect of the present invention, the automatic composite yarn detector comprises a housing holding a pair of electrically conductive contact elements and a piezoelectric tension feeler on the inside, wherein the contact elements are disposed in contact with the yarn and the tension feeler receives the pressure of the yarn, so that the tension of the yarn and its oil content can be respectively detected by the tension feeler and the contact elements. According to another aspect of the present invention, a processing circuit is mounted inside the housing of the automatic composite yarn detector, and adapted to process the electric signals from the tension feeler and the contact elements into corresponding output signals for display through an external display.

DETAILED DESCRIPTION OF THE PREFERRED EMBODIMENT

Figure 3:
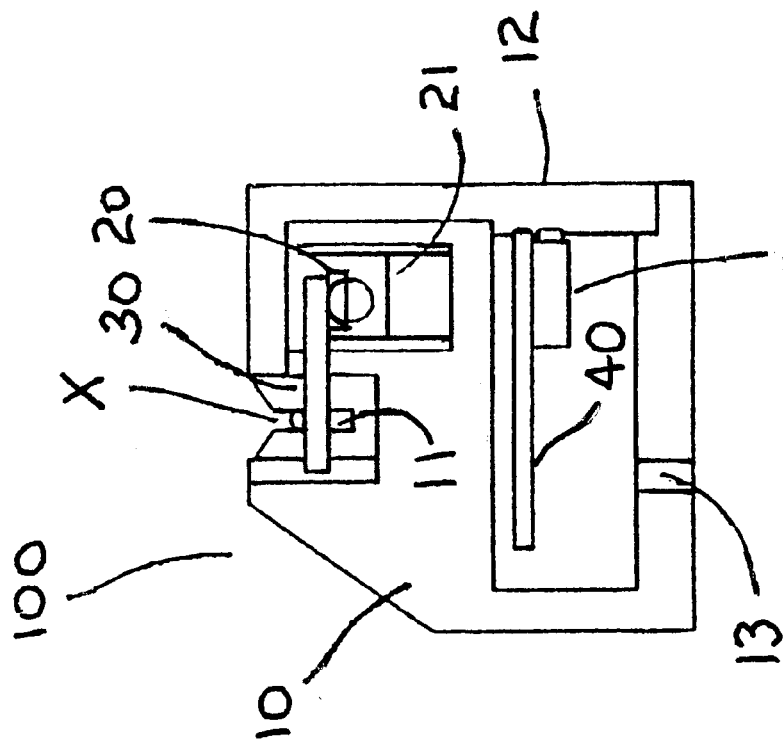
FIG. 3 is a sectional view of the present invention, showing the yarn disposed in contact with the contact elements, and the tension feeler induced.
Figure 1:
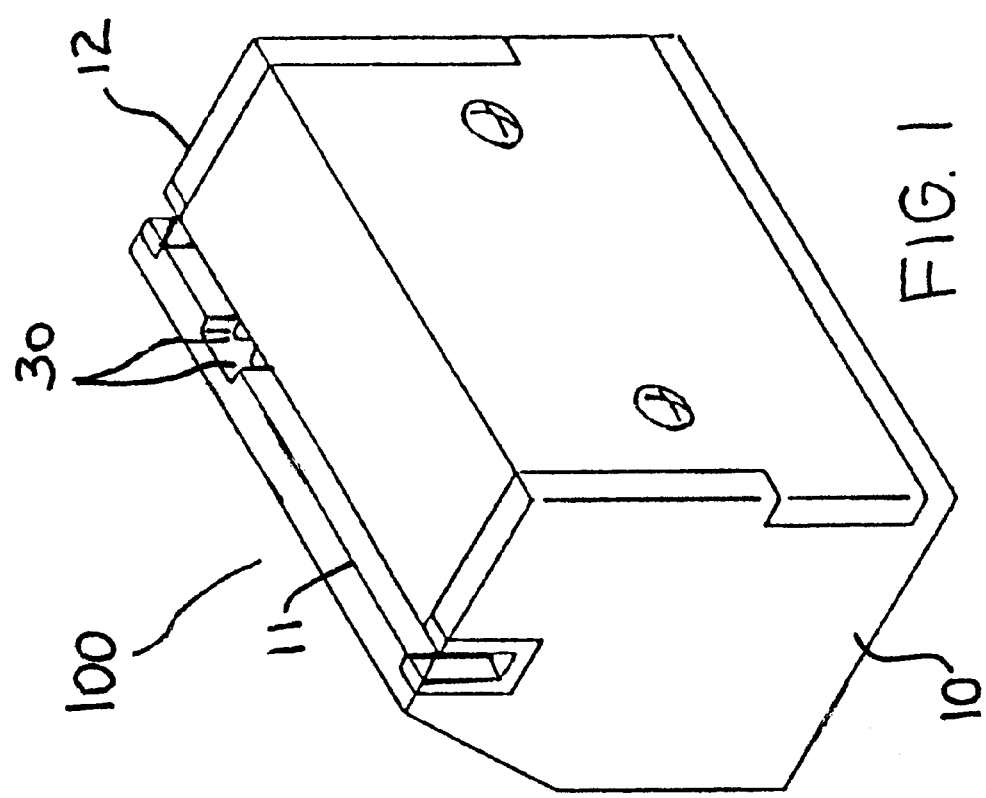
FIG. 1 is an elevational view of an automatic composite yarn detector according to the present invention.
Figure 2:
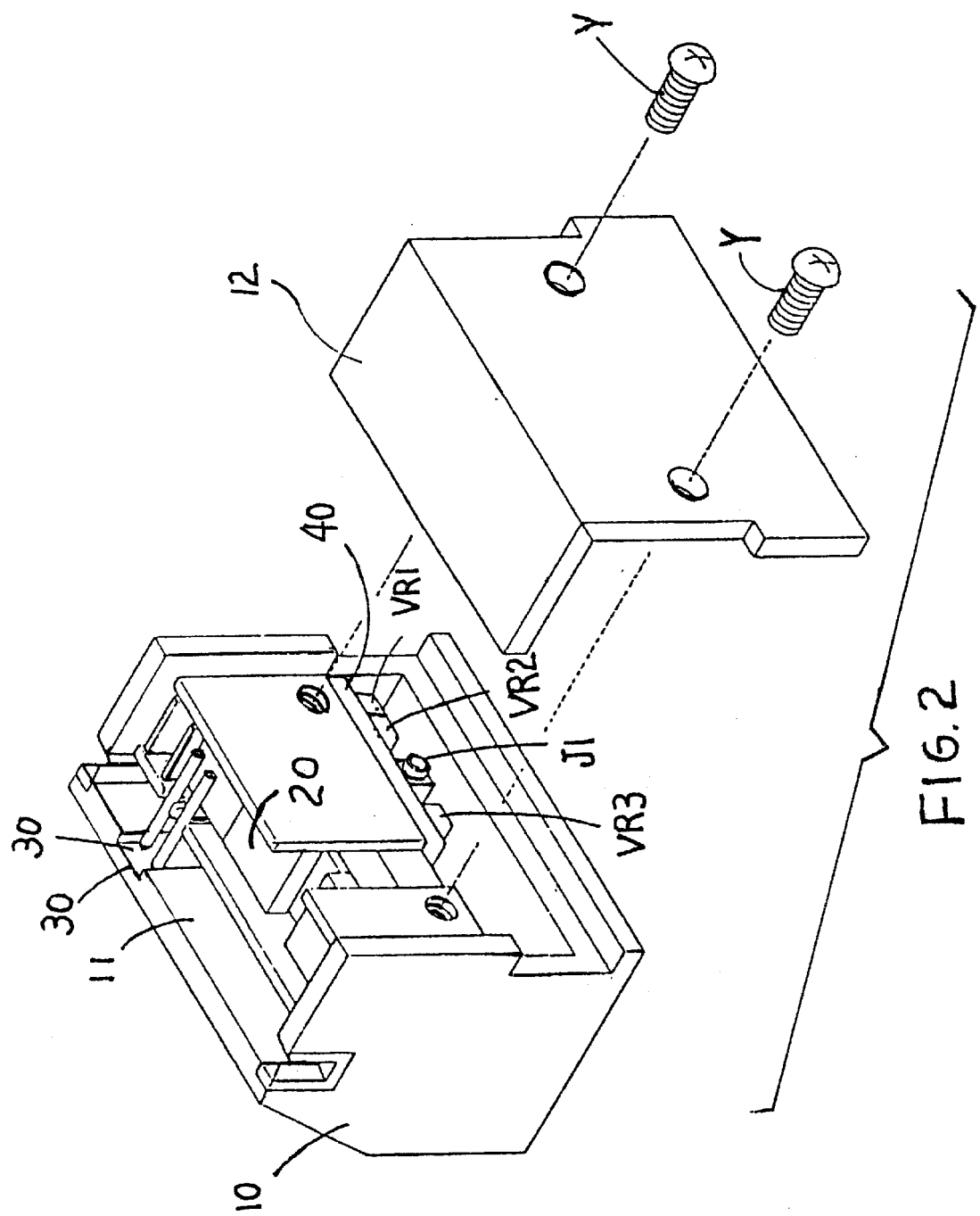
FIG. 2 is an exploded view of the automatic composite yarn detector shown in FIG. 1.

Referring to FIGS. 1 to 3, an automatic composite yarn detector 100 comprises a housing 10 adapted to be installed in the terminal area of a yarn make-up unit of a spinning machine for example a pseudo-twist machine. The housing 10 defines a passage way 11 near its front side through which the yarn (to be tested) X passes (see FIG. 3). A cover 12 is covered on the back side of the housing 10. The cover 12 is fastened to the housing 10 by for example screws Y. A wire hole 13 is provided at the bottom side of the housing 10 through which electric wires pass. A tension feeler 20 is mounted at one side of the passage way 11 within the housing 10, and adapted to detect the tension of the yarn X and to convert it into a corresponding voltage signal. The tension feeler 20 is made in the form of for example a probe coated with a layer of metal by vaporization and fastened to the wall of the housing 10 by a connector 21, which permits the tension feeler 20 to be oscillated horizontally, so as to detect the tension of the yarn X. A pair of contact elements 30 are provided having a respective rear end connected to the tension feeler 20 and a respective front end intersecting the passage way 11 for contacting the yarn X passing through the passage way 11 to detect its oil content so as to provide a corresponding electric signal. A processing circuit 40 is mounted inside the housing 10 to receive signals from the tension feeler 20 and the contact elements 30 corresponding to the tension of the yarn X and its oil content, and then to process the received signals into corresponding digital signals for output through an external display (not shown).

The aforesaid processing circuit 40 comprises a calibration jack J1, a first adjustment device VR1, a second adjustment device VR2, and a third adjustment device VR3. The calibration jack J1 is adapted for connecting to a calibrating apparatus (not shown) through which yarn tension and oil content test parameters are inputted to calibrate the automatic composite yarn detector 100 before the automatic composite yarn detector 100 is delivered out of the factory. The first adjustment device VR1 and the second adjustment device VR2 are adapted to match with the calibration jack J1 for zero the reading of yarn tension parameters and setting the yarn tension detecting range. The third adjustment element VR3 is adapted for adjusting the oil content detecting range.

Figure 4:
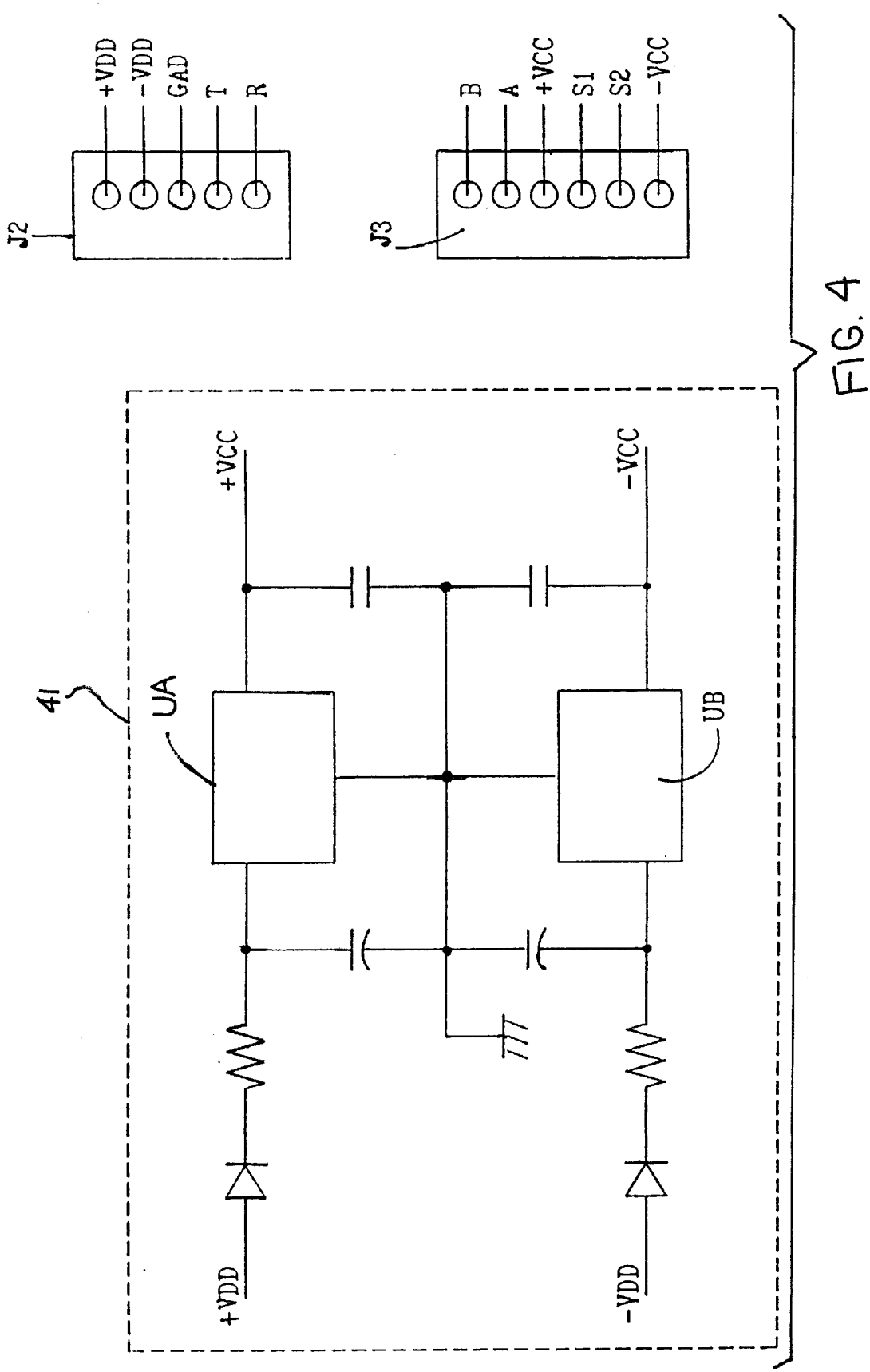
FIG. 4 is a circuit diagram of the present invention (Part I)
Figure 5:
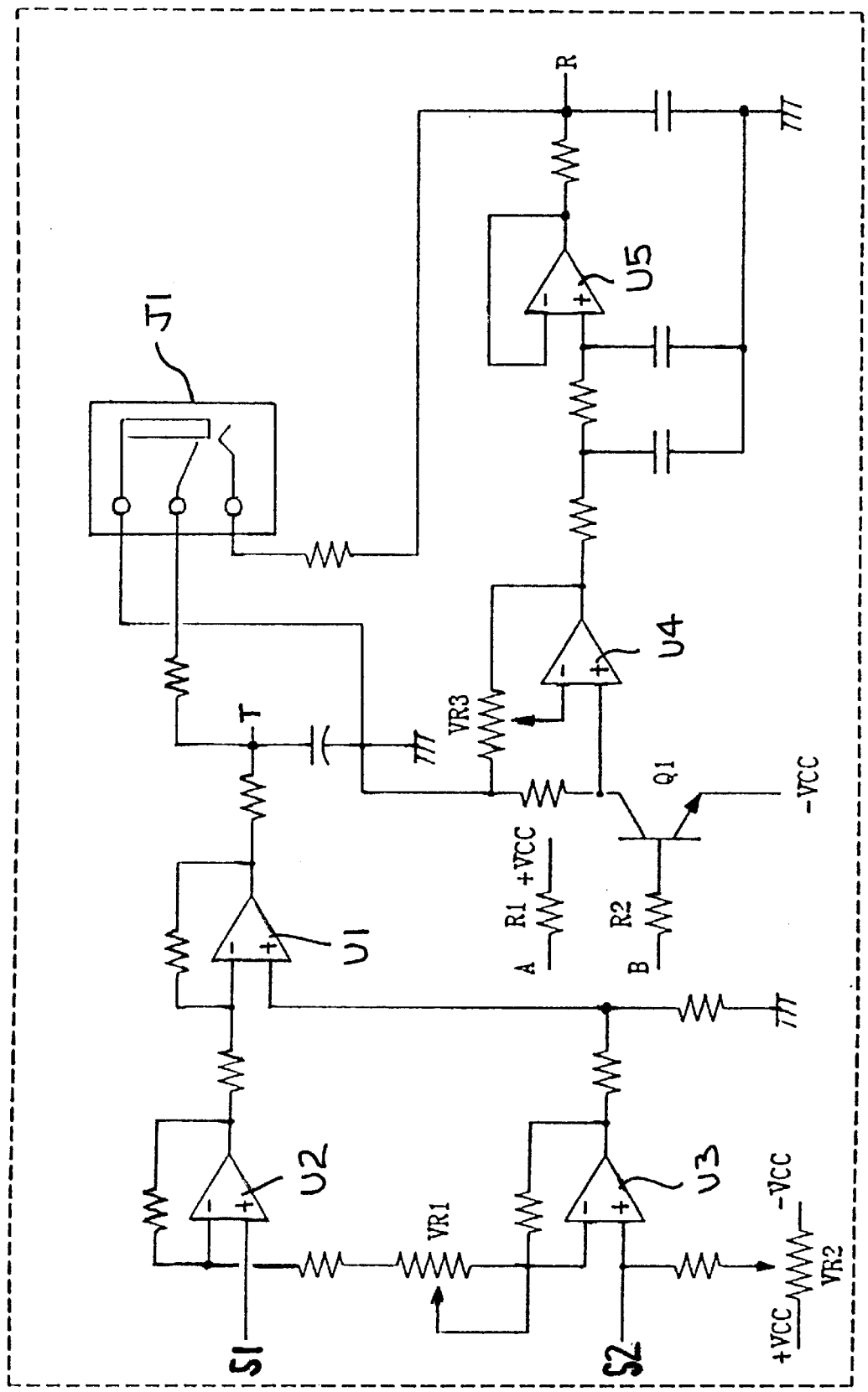
FIG. 5 is a circuit diagram of the present invention (Part II).

Referring to FIGS. 4 and 5 and FIGS. 1 to 3 again, the processing circuit 40 comprises a voltage stabilizer circuit 41 and an operation amplifier circuit 42. The voltage stabilizer circuit 41 comprises two voltage stabilizing ICs UA;UB which convert +VDD and −VDD of a first power supply having a relatively higher voltage into +VCC and −VCC of a second power supply having a relatively lower voltage for the operation amplifier circuit 42. The operation amplifier circuit 42, as shown in FIG. 5, comprises a plurality of operation amplifiers from U1 to U5. The first adjustment device VR1, the second adjustment device VR2 and the third adjustment device VR3 shown in FIG. 2 are represented in FIG. 5 by respective variable resistors. The calibration jack J1 can be made in the form of an earphone jack. Further, the tension detection input terminals S1;S2 shown in FIG. 5 are respectively connected to the signal output terminal of the tension feeler 20 shown in FIGS. 1 to 3 to detect the pressure applied to the contact elements 30 by the yarn X passing through the passage way 11. When the contact elements 30 receive a pressure from the yarn X passing through the passage way 11, the tension feeler 20 is forced to displace, causing a voltage signal to be produced and provided to an amplifier loop, which is formed of the first, second and third operation amplifiers U1;U2;U3. After processing through the amplifier loop U1;U2;U3, the processed signal is outputted through the first output terminal T to the detector 100 or the external display. Further, the oil content detection input terminals A;B are respectively connected to the contact elements 30. One of the contact elements 30 is connected to +VCC of the second power supply through a resistor R1, and the other of the contact elements 30 is connected to the base of a transistor Q1 through a resistor R2. When yarn surface of the yarn X contacts the surface of the contact elements 30, a micro current is produced (because oil carried on the surface of the yarn X is electrically conductive) and transmitted from one contact element 30 to the other through the surface of the yarn X, i.e., a micro current is transmitted from the oil content detection input terminal A to the oil content detection output terminal B. The micro current is then pre-amplified by the transistor Q1, and then processed by a posterior amplifier loop, which is comprised of the fourth and fifth operation amplifiers U4;U5, and then transmitted through the second output terminal R to the detector 100 or the external display, therefore the tension and oil content of the yarn X are simultaneously detected.

In order to facilitate the installation of internal and external electric wires, +VDD and −VDD of first power supply, +VCC and −VCC of second power supply, tension detection input terminals S1;S2, oil content detection terminals A;B, first output terminal T and second output terminal R are respectively mounted in first connector J2 and second connector J3.

It is to be understood that the drawings are designed for purposes of illustration only, and are not intended as a definition of the limits and scope of the invention disclosed.

What the invention claimed is:

1. An automatic composite yarn detector comprising:

a housing having a passageway through which the yarn to be tested passes;

a tension feeler pivoted to said housing on the inside and adapted to detect the tension of said yarn through two electrically conductive contact elements and to provide an output signal corresponding to its detection result;

said two electrically conductive contact elements having a respective rear end connected to said tension feeler and a respective front end intersecting said passageway for receiving a pressure from said yarn and detecting an oil content from it, permitting the received pressure to be transmitted to said tension feeler and the detected oil content signal to be transmitted to a processing circuit; and said processing circuit mounted inside said housing and adapted to process the output signal of said tension feeler and the detected oil content signal of said electrically conductive contact elements into corresponding output signals for display through an external display.

2. The automatic composite yarn detector of claim 1, wherein said housing has a bottom wire hole through which electric wires pass.

3. The automatic composite yarn detector of claim 1, wherein said tension feeler is a probe coated with a layer of metal by vaporization.

4. The automatic composite yarn detector of claim 1, wherein the output signal of said tension feeler is a voltage signal.

5. The automatic composite yarn detector of claim 1, wherein said two electrically conductive contact elements include a first contact element connected to power supply, and a second contact element connected to said processing circuit and arranged in parallel to said first contact element, said second contact element being induced to provide an electric output signal to said processing circuit by the oil content of said yarn when said yarn passes through said passageway over said two electrically conductive contact elements.

6. The automatic composite yarn detector of claim 1, wherein said processing circuit is comprised of a voltage stabilizer circuit and an operation amplifier circuit.

7. The automatic composite yarn detector of claim 6, wherein said operation amplifier circuit is comprised of a plurality of operation amplifiers.

8. The automatic composite yarn detector of claim 6, wherein said operation amplifier circuit comprises a calibration jack, a first adjustment device, a second adjustment device, and a third adjustment device.

9. The automatic composite yarn detector of claim 8, wherein said calibration jack is for connection to an external calibration apparatus; said first adjustment device, said second adjustment device and said third adjustment device are adapted for adjusting the tension detecting range and the oil content detecting range.

10. The automatic composite yarn detector of claim 8, wherein said calibration jack is made in the form of an earphone; said first adjustment device, said second adjustment device and said third adjustment device are variable resistors.

* * * * *